(12) United States Patent
Chen et al.

(10) Patent No.: US 8,277,634 B2
(45) Date of Patent: Oct. 2, 2012

(54) ELECTROLYTIC WATER TREATMENT DEVICE HAVING SINTERED NANOPARTICLE COATED ELECTRODE AND METHOD FOR MAKING ACID OR BASIC WATER THEREWITH

(75) Inventors: Yongge Chen, Guangzhou (CN); Roberto De Noni, Fregona (IT)

(73) Assignee: APR Nanotechnologies S.A., Balerna (CH)

( * ) Notice: Subject to any disclaimer, the term of this patent is extended or adjusted under 35 U.S.C. 154(b) by 1035 days.

(21) Appl. No.: 12/091,765

(22) PCT Filed: Oct. 23, 2006

(86) PCT No.: PCT/EP2006/067676
§ 371 (c)(1),
(2), (4) Date: Jul. 1, 2008

(87) PCT Pub. No.: WO2007/048772
PCT Pub. Date: May 3, 2007

(65) Prior Publication Data
US 2008/0292717 A1    Nov. 27, 2008

(30) Foreign Application Priority Data

Oct. 28, 2005 (IT) .............................. PN2005A0079
Jun. 28, 2006 (IT) .............................. MI2006A1252

(51) Int. Cl.
*C02F 1/461* (2006.01)
*C25B 1/24* (2006.01)
*C25B 1/22* (2006.01)

(52) U.S. Cl. ........ 205/687; 205/618; 205/620; 205/622; 205/625; 205/742

(58) Field of Classification Search .......... 205/618–622, 205/625, 687, 742
See application file for complete search history.

(56) References Cited

U.S. PATENT DOCUMENTS 3,632,498 A * 1/1972 Beer ........................ 204/290.12
3,948,751 A * 4/1976 Bianchi et al. ........... 204/290.03
4,146,438 A * 3/1979 de Nora et al. ................ 205/43

(Continued)

FOREIGN PATENT DOCUMENTS
EP         0933332        8/1999

(Continued)

OTHER PUBLICATIONS

Anonymous, "Aquatech Amsterdam 2006 Press Information," [online] Aug. 28, 2006, URL:www.amsterdam.aquatechtrade.com/_upload/aquatech2006/docs/Noviteiten_supplement_ENG.doc.

(Continued)

*Primary Examiner* — Arlen Soderquist
(74) *Attorney, Agent, or Firm* — Arnall Golden Gregory LLP; Clark G. Sullivan

(57) ABSTRACT

A highly stable aqueous solution having a molecular cluster with dimensions which are small enough to ensure substantial chemical-physical stability thereof for a relatively long time. To prepare the solution a fluid treatment device is used, which comprises at least one chamber (7) and at least one anode (4) and one cathode (3) arranged in the chamber (7). The anode (4) and cathode (3) are at least partly made of a first metallic material. At least one of the at least one cathode (3) and anode (4) comprises a coating of nanoparticles (5) of a second metallic material.

13 Claims, 5 Drawing Sheets

U.S. PATENT DOCUMENTS

| | | | |
|---|---|---|---|
| 4,302,321 A * | 11/1981 | deNora et al. ........... | 204/291 |
| 4,564,434 A * | 1/1986 | Busse-Machukas et al. ........... | 204/290.13 |
| 5,234,563 A | 8/1993 | Arai et al. | |
| 5,334,383 A | 8/1994 | Morrow | |
| 5,445,722 A | 8/1995 | Yamaguti et al. | |
| 5,474,662 A | 12/1995 | Miyamae | |
| 5,507,932 A | 4/1996 | Robinson | |
| 5,510,009 A | 4/1996 | Arai et al. | |
| 5,560,816 A | 10/1996 | Robinson | |
| 5,587,058 A * | 12/1996 | Gorodetsky et al. ...... | 204/290.09 |
| 5,589,052 A | 12/1996 | Shimamune et al. | |
| 5,593,554 A | 1/1997 | Yamanaka et al. | |
| 5,616,221 A | 4/1997 | Aoki et al. | |
| 5,622,828 A | 4/1997 | Parma et al. | |
| 5,622,848 A | 4/1997 | Morrow | |
| 5,674,537 A | 10/1997 | Morrow | |
| 5,711,950 A | 1/1998 | Lorenzen | |
| 5,731,008 A | 3/1998 | Morrow | |
| 5,759,489 A | 6/1998 | Miura et al. | |
| 5,824,353 A | 10/1998 | Tsunoda et al. | |
| 5,900,127 A | 5/1999 | Iida et al. | |
| 5,965,009 A | 10/1999 | Shimamune et al. | |
| 5,980,703 A | 11/1999 | Yamada et al. | |
| 6,033,678 A | 3/2000 | Lorenzen | |
| 6,093,292 A | 7/2000 | Akiyama | |
| 6,126,796 A | 10/2000 | Shimamune et al. | |
| 6,126,810 A | 10/2000 | Fricker et al. | |
| 6,174,419 B1 | 1/2001 | Akiyama | |
| 6,207,201 B1 | 3/2001 | Piacenza | |
| 6,235,186 B1 | 5/2001 | Tanaka et al. | |
| 6,258,222 B1 | 7/2001 | Nakamura et al. | |
| 6,296,744 B1 | 10/2001 | Djeiranishvili et al. | |
| 6,426,066 B1 | 7/2002 | Najafi et al. | |
| 6,464,845 B2 | 10/2002 | Shirota et al. | |
| 6,527,940 B1 | 3/2003 | Shimamune et al. | |
| 6,632,347 B1 | 10/2003 | Buckley et al. | |
| 7,090,753 B2 | 8/2006 | Sumita | |
| 7,276,255 B2 | 10/2007 | Selkon | |
| 7,291,314 B2 | 11/2007 | Paskalov et al. | |
| 7,303,660 B2 | 12/2007 | Buckley et al. | |
| 7,323,118 B2 | 1/2008 | Calderon | |
| 7,393,522 B2 | 7/2008 | Najafi et al. | |
| 7,442,288 B2 | 10/2008 | Sumita | |
| 2002/0119093 A1* | 8/2002 | Murayama et al. ........... | 423/592 |
| 2002/0134691 A1 | 9/2002 | Satoh et al. | |
| 2003/0185704 A1 | 10/2003 | Bernard et al. | |
| 2003/0209437 A1* | 11/2003 | McInerney et al. ........... | 204/515 |
| 2004/0069618 A1* | 4/2004 | Paskalov et al. ............ | 204/193 |
| 2004/0258836 A1 | 12/2004 | Besenhard | |
| 2005/0067300 A1* | 3/2005 | Tremblay ..................... | 205/742 |
| 2005/0139808 A1 | 6/2005 | Alimi | |
| 2005/0142157 A1 | 6/2005 | Alimi | |
| 2005/0196462 A1 | 9/2005 | Alimi | |
| 2006/0235350 A1 | 10/2006 | Alimi et al. | |
| 2006/0241546 A1 | 10/2006 | Alimi | |
| 2006/0249375 A1 | 11/2006 | Aoun et al. | |
| 2006/0253060 A1 | 11/2006 | Alimi | |
| 2006/0275387 A1 | 12/2006 | Bagley | |
| 2007/0017820 A1 | 1/2007 | Anderson et al. | |
| 2007/0051640 A1 | 3/2007 | Bellamy | |
| 2007/0173755 A1 | 7/2007 | Alimi et al. | |
| 2007/0196357 A1 | 8/2007 | Alimi et al. | |
| 2007/0196434 A1 | 8/2007 | Alimi et al. | |
| 2007/0292744 A1* | 12/2007 | Lopez et al. ..................... | 429/44 |
| 2009/0181107 A1 | 7/2009 | Buckley et al. | |
| 2009/0221989 A1 | 9/2009 | Najafi et al. | |
| 2009/0258083 A1 | 10/2009 | Calderon | |
| 2010/0119616 A1* | 5/2010 | Chen et al. ..................... | 424/600 |
| 2010/0330204 A1* | 12/2010 | Chen et al. ..................... | 424/665 |

FOREIGN PATENT DOCUMENTS

| | | |
|---|---|---|
| EP | 1007478 | 8/2003 |
| EP | 1036861 B1 | 10/2003 |
| EP | 1600426 | 11/2005 |
| EP | 1103264 | 5/2007 |
| EP | 1551770 | 3/2010 |
| JP | 04235904 | 8/1992 |
| JP | 06126287 | 5/1994 |
| JP | 11035472 | 2/1999 |
| JP | 2000229815 | 8/2000 |
| JP | 2001096272 | 4/2001 |
| WO | WO97/19707 | 6/1997 |
| WO | WO2004/078654 | 9/2004 |
| WO | WO2005/065383 | 7/2005 |
| WO | WO2007/048772 | 5/2007 |
| WO | WO2008/091032 | 7/2008 |
| WO | WO2008/131936 | 11/2008 |

OTHER PUBLICATIONS

"BioCera® Alkaline Purifier" [online], URL:http://www.biocera.co.kr/eng/Antioxidant_Alkaline_Water_Filter.htm.

Dermacyn® Wound Care, [online], Oculus Innovative Sciences, URL:www.oculusis.com.

Fenner, Dunja Corinne, "Antimicrobial activity of electrolyzed oxidizing water using standard in-vitro test procedures for the evaluation of chemical disinfectants", [online] Inaugural-Dissertation, Zurich Oct. 6, 2005, URL:http://www.water4u.net/file_download.php?filename=63ff8dbc4bb2121cc20add56549dcbe2.

Hayashi, Hidemitsu, "Benefits of Alkaline, Ionized Water" [online] Oct. 6, 2005, URL:http://www.ionizers.org/water.html.

Hayashi, Hideaki, et al., Artificial Organs, "Successful Treatment of Mediastinitis after Cardiovascular Surgery Using Electrolyzed Strong Acid Aqueous Solution," vol. 21, p. 39-42, 1997.

Hsu, Shun-Yao, et al., Journal of Food Engineering, "Effects of storage conditions on chemical and physical properties of electrolyzed oxidizing water," vol. 65, p. 465-471, 2004.

Kim, Yong Jeong, et al., "Suppression of cobalt dissolution from the $LiCoO_2$ cathodes with various metal-oxide coating", Database Compendex [online] Dec. 2003.

Kim, Tae-Joon, et al., Electrochimica Acta, "Enhanced electrochemical properties of $SnO_2$ anode by $AlPO_4$ coating", vol. 49, No. 25, p. 4405-4410, 2004.

Len, Soo-Voon, et al., J. of Agric. Food Chem., "Effects of Storage Conditions and pH on Chlorine Loss in Electrolyzed Oxidizing (EO) Water," vol. 50, p. 209-212, 2002.

Nakagawara, Shunji, et al., Analytical Sciences, "Spectroscopic Characterization and the pH Dependence of Bactericidal Activity of the Aqueous Chlorine Solution," vol. 14, p. 691-698, 1998.

Venkitanarayana, Kumar S., et al., "Efficacy of Electrolyzed Oxidizing Water for Inactivating *Escherichia coli* O157:H7, *Salmonella enteritidis*, and *Listeria monocytogens*," Applied Enviro. Microbiology, vol. 65, No. 9, p. 4276-4279, 1999.

Yang, Gordon C.C., et al., J. of Membrane Science, "Reclamation of high quality water from treating CMP wastewater by a novel crossflow electrofiltration/electrodialysis process," vol. 233, p. 151-159, 2004.

* cited by examiner

ELECTROLYTIC WATER TREATMENT DEVICE HAVING SINTERED NANOPARTICLE COATED ELECTRODE AND METHOD FOR MAKING ACID OR BASIC WATER THEREWITH

TECHNICAL FIELD

The present invention lies in the field of disinfectants and relates to a highly stable acid aqueous composition, to a method for producing said composition, to a device which is used in the context of this method, to an apparatus which comprises said device, and to the corresponding uses of said composition.

BACKGROUND ART

It is known that aqueous solutions of salts, particularly sodium chloride, as a consequence of an electrolytic treatment, are split into two liquid products, one having basic and reducing characteristics (generally known as cathode water or basic water) and another (generally termed anode water or acid water) having acid and oxidizing characteristics. Anode water, thanks to its high oxidizing power, is known for use as a disinfectant product in the food, medical and cosmetic field.

Conventional anode waters suffer the acknowledged drawback of having very limited preservation. A few days after preparation, the product in fact generally tends to degrade and lose its properties. Known electrolytic acid waters, therefore, must be prepared and used substantially on the spot. Accordingly, the commercial utilization of the product in itself is extremely disadvantageous, since the shelf life of any ready-made packages is dramatically limited.

Another drawback of conventional electrolytic acid waters resides in their limited capacity for skin penetration, which makes them substantially ineffective in disinfecting non-superficial impurities.

Finally, known electrolytic acid waters tend to have a high amount of chlorine, requiring for their use specific solutions whose implementation, however, is within the reach only of specialized technicians.

DISCLOSURE OF THE INVENTION

The aim of the present invention is therefore to provide an electrolytic acid water, particularly as a disinfectant composition, which overcomes the drawbacks of the background art.

Within this aim, one of the objects of the present invention is to provide an electrolytic acid water which has high stability over time of its disinfectant power, a low production cost and easy preparation.

Another object of the invention is to provide an electrolytic acid water as defined above which has a high capacity for penetration for example in the deep layers of the skin and which, after its application, leaves a low residue of elements of known toxicity, so as to have a low index of toxicity for humans and animals.

Another object is to provide a method for preparing an electrolytic acid water as defined above.

Another object is to provide a device which is used in the context of a method for preparing an electrolytic acid water as defined above.

Another object is to provide an apparatus for providing a method for preparing an electrolytic acid water as defined above.

Still another object is to provide a use of an electrolytic acid water as defined above.

This aim and these and other objects are achieved by an electrode, particularly for electrolytic cells, characterized in that it comprises a surface coating which comprises nanoparticles of one or more metals.

The aim and objects of the invention are also achieved by a device particularly for the electrolytic treatment of a fluid, which comprises at least one chamber for the electrolytic treatment of said fluid and at least one pair of electrodes for each chamber, said electrodes being arranged within said at least one chamber, wherein the device is characterized in that at least one of the electrodes that are present is as defined above.

The aim and objects of the invention are also achieved by an apparatus particularly for the electrolytic treatment of a fluid, characterized in that it comprises a device as defined above.

The aim and objects of the invention are also achieved by a method for providing the electrolysis of a fluid, which comprises a step a) of subjecting to electrolysis a given quantity of a fluid inside a device as defined above.

The aim and objects of the invention are also achieved by an acid water, particularly as a sanitizing agent, which can be obtained with a method for electrolysis as defined above and wherein the fluid subjected to electrolysis is water.

The aim and objects of the invention are also achieved by a composition particularly for sanitizing a substrate, which comprises an acid water as defined above and one or more ingredients selected from the group that consists of:

i) excipients and carriers which are pharmaceutically acceptable for preparing pharmaceutical compositions for human or animal use, ii) excipients and carriers which are cosmetically acceptable for preparing cosmetic compositions for human or animal use, iii) excipients and carriers used in the food sector to prepare disinfectant compositions, and iv) excipients and carriers used in the agricultural sector to prepare antiparasitic or fungicide compositions.

The aim and objects of the invention are also achieved by a kit which comprises an electrolytic acid water as defined above and means for applying it to a substrate.

The aim and objects of the invention are also achieved by the use of an acid water as defined above to prepare a medication for treating and preventing superficial or deep skin disorders or lesions of the human or animal body.

The aim and objects of the invention are also achieved by the use of an electrolytic acid water as defined above to sanitize a substrate.

The aim and objects of the invention are also achieved by the use of an acid water as defined above for cosmetic treatment of the human or animal body or of isolated parts thereof.

The aim and objects of the invention are also achieved by the use of an acid water as defined above to carry preparations suitable for bone reconstruction.

The aim and objects of the invention are also achieved by the use of an electrolytic acid water as defined above to rehydrate dehydrated human or animal tissues for reimplantation.

It is understood that any characteristic which is cited with reference to just one of the aspects of the invention but which can also refer to other aspects is to be considered equally valid with reference to these other aspects although it is not repeated explicitly.

BRIEF DESCRIPTION OF THE DRAWINGS

Further characteristics and advantages of the invention will become better apparent from the description of the following FIGS. 1 to 5, which are provided by way of non-limiting example and wherein.

WAYS OF CARRYING OUT THE INVENTION

Figure 1:
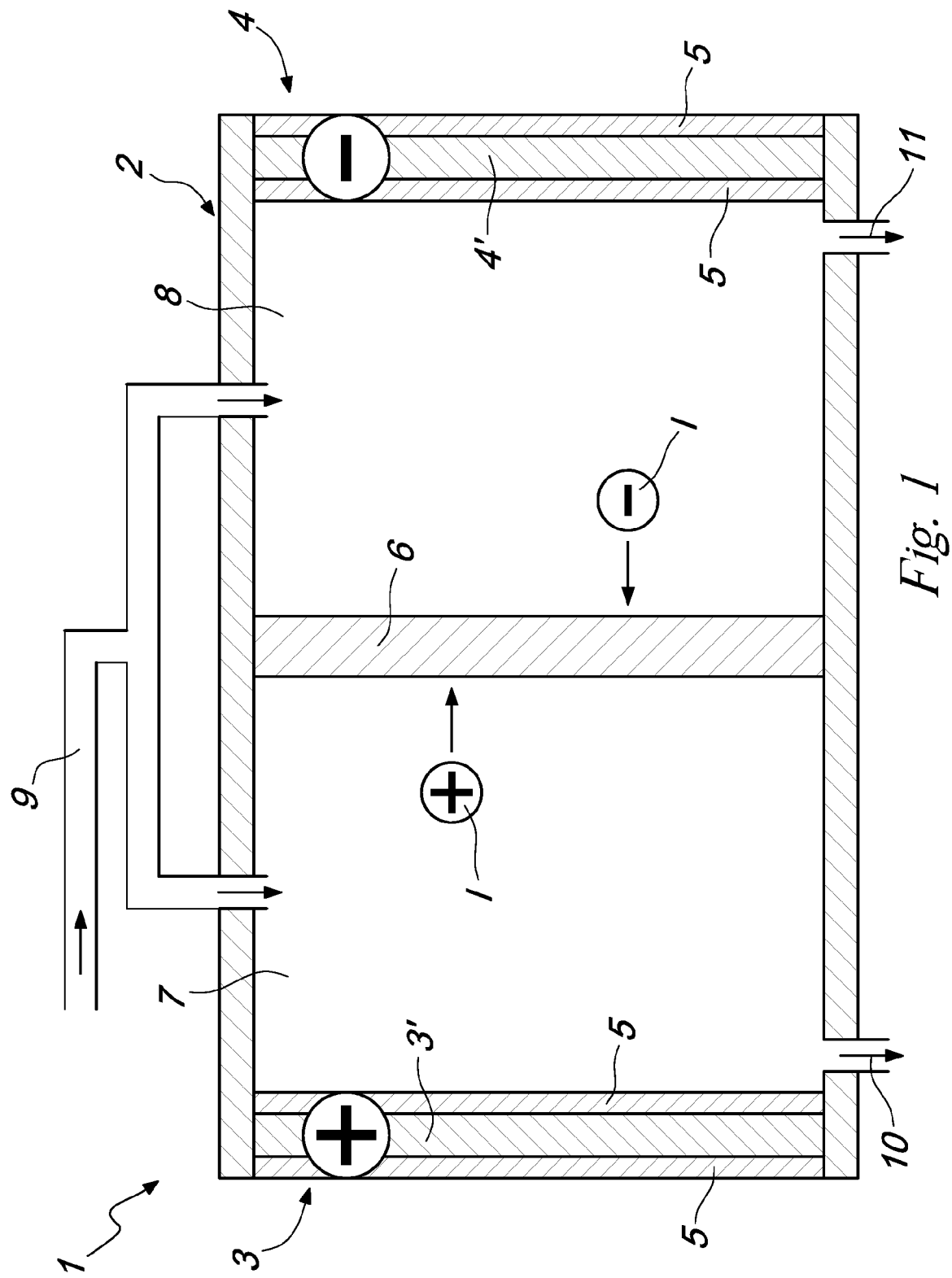
FIG. 1 is a schematic view of the electrolytic device 1 according to the invention, which comprises an electrolysis chamber 2 and two electrodes 3 and 4.
Figure 2:
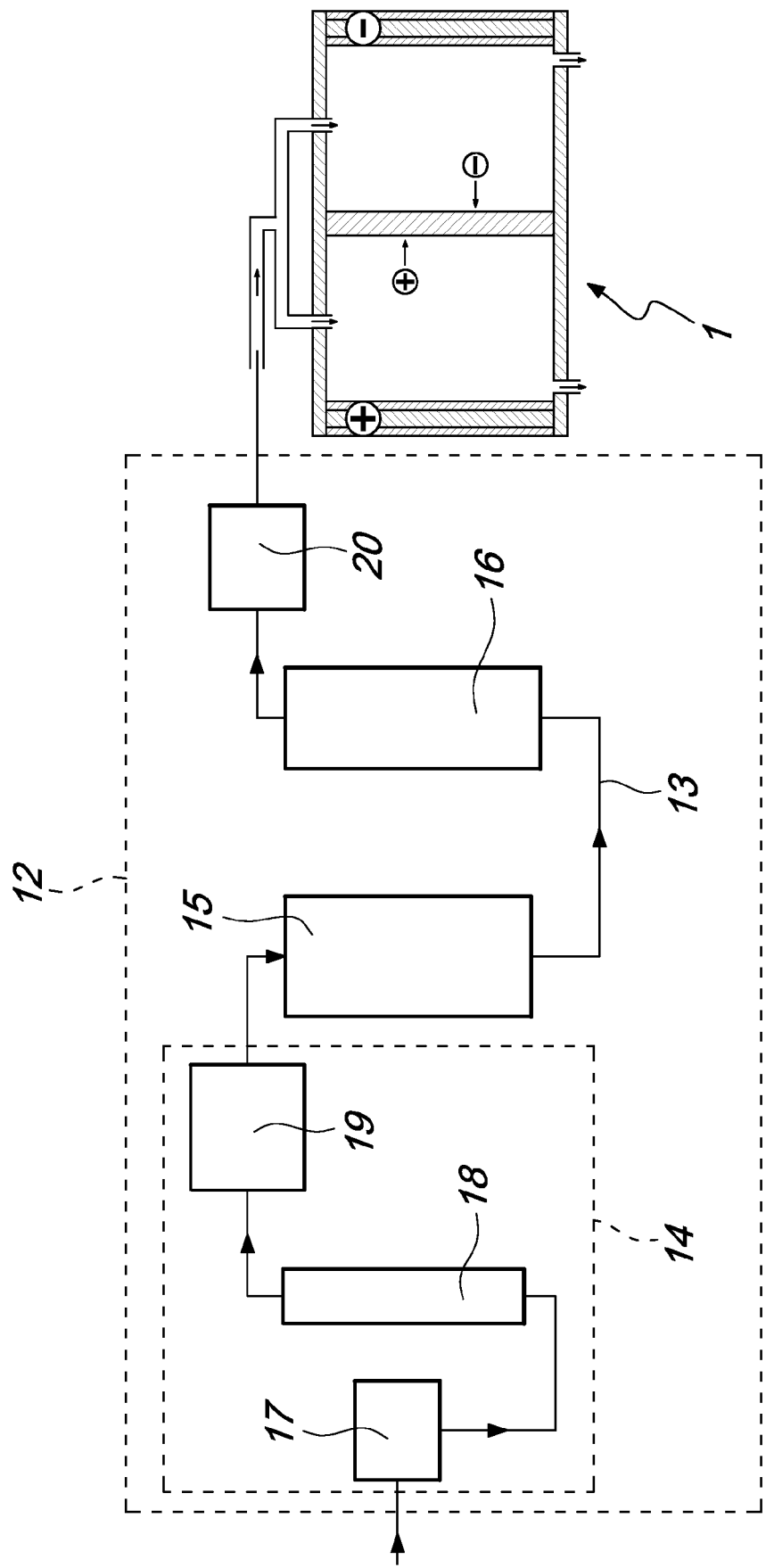
FIG. 2 is a schematic view of the apparatus according to the invention, comprising an electrolytic device 1 according to FIG. 1.

The term "fluid" is used to reference any pure fluid, solution or suspension which is capable of producing a non-spontaneous chemical reaction if subjected to electrolysis. One highly preferred fluid is water. The term "water" is used to reference any type of water, such as tap water, filtered water, deionized water, distilled water. A water which can be treated with the invention can have a higher percentage of solid pollutants in solution than waters which can be treated with conventional devices, by virtue of the possibility to provide a continuous reversal of polarity between the electrodes (polarity swapping, as defined below). Any polluting solutes, if electrically charged, would in fact be attracted by the opposite pole, forming a flow which would rapidly clog the pores of any membrane provided in the electrolytic device, blocking the process. On the contrary, continuous and rapid reversal of polarity does not produce any flow and the pores of the membrane, if provided, remain clean and efficient.

Once subjected to electrolysis, the water separates into two liquid fractions, which for the sake of simplicity are referenced here as anode water or acid water and as cathode water or basic water.

The characteristics and advantages of the present invention in all of its aspects are now described exclusively in relation to the highly preferred embodiment in which the fluid to be subjected to electrolysis is water. However, on the basis of the information and details provided hereinafter, it will be immediately evident to the person skilled in the art that it is possible to achieve the same advantages also with the electrolysis of fluids other than water.

In a first aspect, the invention relates to an electrode 3 or 4, particularly for electrolytic cells, characterized in that it comprises a surface coating 5 which comprises nanoparticles of one or more metals.

In a preferred embodiment, the electrode, which as will become apparent can be used equally as an anode and as a cathode, comprises a core 3' or 4' which is made of a metallic material, a nonmetallic material or combinations thereof.

If the core is made of metallic material, it can be made for example of an alloy of titanium and platinum or an alloy of steel and graphite.

If the core is made of a nonmetallic material, it can be made for example of graphite.

The core may also comprise different layers, such as for example a core made of graphite which is coated with an outer layer of metal, for example titanium. The term "metal" references both a metal and chemical compounds which comprise said metal, such as its oxides. A preferred core is made of $TiO_2$.

The electrode according to the invention is characterized with respect to known electrodes substantially due to the presence of a nanometer covering 5 (hereinafter also referenced as coating) which is extremely smooth, i.e., a layer for covering the core which includes metallic nanoparticles.

The metals of which the nanoparticles of the coating 5 are made are selected preferably among one or more of titanium, iridium, yttrium, ruthenium, zinc, zirconium and platinum and compounds thereof. Preferred metal compounds are oxides of the mentioned metals. A preferred coating 5 comprises $ZrO_2$, $ZnO$, $Ru_2O_3$, $IrO_2$ and $Y_2O_3$. Preferably, the various metals are used in powder form.

In one embodiment, the coating 5 can also comprise a nonmetallic carrier material, for example particles of one or more polymers. The polymer can be synthetic (such as for example plastics, acrylic polymers, et cetera) or partly synthetic (such as for example modified celluloses, modified starches, et cetera).

The metallic nanoparticles comprised within the coating 5 are preferably used in powder form. As regards the size distribution within the powder, preferably an amount at least equal to 80% by weight of the particles that are present in the powder, more preferably at least equal to 85%, has a particle diameter ranging from 60 to 80 nm.

In another aspect, the invention relates to a method for obtaining an electrode 3 or 4 as defined above.

The coating 5 of the invention can be provided by means of nanotechnology techniques which are known to a person skilled in the art and are adapted to produce a smooth surface, for example by sintering the powder or the mixtures of metallic nanopowders.

The individual metals in powder form can be applied to the electrode so as to produce the coating: 1) as a preformed mixture, and/or 2) in the form of discrete layers which are applied sequentially and mutually superimposed and wherein each layer consists of a single metal, and/or 3) in the form of discrete layers which are applied sequentially and mutually superimposed and in which each layer consists of two or more metals but not simultaneously of all the metals that are present in the coating.

In a preferred embodiment, the method comprises the step (A) of preparing the coating of the electrode by sintering powders of nanoparticles of one or more metals as defined above directly on the core of the electrode. Preferably, step (A) comprises the following steps to be performed in the order in which they are listed here:

(A1) preparing one or more powders of metallic nanoparticles as defined above, (A2) dissolving the one or more powders of nanoparticles in a suitable solvent and in at least such a quantity as to be able to dissolve all the powder to be applied, obtaining one or more solutions, and (A3) sintering the one or more solutions obtained in the preceding step on a metal plate, preferably passivated on its surface, which will form the core of the electrode.

Preferably:
the one or more powders of metallic nanoparticles of step
(A1) is a combination of powders of $ZrO_2$, $ZnO$, $Ru_2O_3$, $IrO_2$ and $Y_2O_3$, advantageously obtained by hydrothermal chemical processing, wherein in each powder at least 80% and more preferably at least 85% by weight of the particles have a diameter ranging from 60 to 80 nm;

the solvent of step (A2) in which each powder is dissolved is a 30% solution by weight of hydrochloric acid in water, in at least such an amount as to be able to dissolve all the powder to be applied, step (A3) consists in sintering the aqueous solutions of hydrochloric acid obtained from step A(2) on both faces of a $TiO_2$ plate which is passivated on its surface and has a thickness ranging from 0.15 to 0.35 mm, wherein sintering occurs according to the following steps:

| Step | Solution | Dosage per unit surface | Sintering time (min) | Sintering temperature (°C.) |
|---|---|---|---|---|
| 1 | $IrO_2$ | 0.2 g/m² | 45 | 450 |
| 2 | $Ru_2O_3$ | 0.2 g/m² | 45 | 450 |
| 3 | $ZnO + Y_2O_3$ (Y at 2 mol) | 0.15 g/m² | 60 | 550 |
| 4 | $IrO_2$ | 0.25 g/m² | 45 | 450 |
| 5 | $Ru_2O_3$ | 0.25 g/m² | 60 | 550 |
| 6 | $ZrO_2 + Y_2O_3$ (Y at 3 mol) | 0.1 g/m² | 60 | 550 |
| 7 | $Ru_2O_3$ | 0.15 g/m² | 60 | 550 |
| 8 | $IrO_2$ | 0.15 g/m² | 60 | 550 |
| 9 | $IrO_2 + Ru_2O_3$ | 0.15 g/m² + 0.15 g/m² | 60 | 600 |
| 10 | $ZrO_2 + Y_2O_3$ (Y at 3 mol) | 0.1 g/m² | 60 | 600 |
| 11 | $IrO_2 + Ru_2O_3$ | 0.15 g/m² + 0.15 g/m² | 60 | 600 |

Resorting to multiple sintering steps has been found to be particularly useful in order to eliminate any roughness from the surface of the electrode and obtain an extremely hard and smooth surface.

An electrode as defined above, used as part of a device for providing the electrolysis of water, produces the following advantages:

more efficient electrolysis, in that there is a lower consumption of salts such as NaCl, used conventionally to accelerate the electrolysis of low-conductivity fluids such as water;

in the highly preferred embodiment in which both electrodes are electrodes according to the invention, the possibility to provide a continuous change of polarity of the electrodes ("polarity swapping"). The sudden change of polarity allows the charged particles that are present in the fluid subjected to electrolysis to circulate in both directions instead of just in one (forced by the charge of the particles and by the unchangeable sign of the electrodes), thus avoiding the forming of deposit-producing masses at the level of the electrodes and thus keeping their surface clean and their efficiency at the maximum level. Moreover, if a semipermeable membrane 6 is provided within the electrolytic cell and divides the two anode and cathode half-chambers, the change of polarity avoids the clogging of the pores of said membrane, extending the life of the device;

the presence of a nanometer coating 5 determines an accumulation of charge by the upper electrode to more than 100% with respect to conventional electrodes. This allows to provide a qualitatively and quantitatively different electrolysis at significantly higher potentials, with the effect of, for example, reducing the size of molecular clusters;

the obtainment of a very high consistency, smoothness and surface density, aspects which avoid the solubilization of the electrode itself or the forming of sediments on its surface, which would then occur in the acid and basic water fractions.

The same aspects are also the basis for the substantially nil release of heavy metals and other compounds which constitute the surface and core of the electrode within the acid and basic water fractions. As will be mentioned also hereafter, the absence of heavy metals in the acid water leads to an amazing stability thereof over time, with preservation of characteristics such as ORP, pH and molecular cluster size. This stability is unknown to known equivalent products.

The same aspects are also the basis for the minimal maintenance required by the electrode, which can be changed with a significantly lower frequency than known electrodes, reducing costs and increasing ease of production;

the possibility to obtain quantum effects (known in the literature also by the term "nanoeffects") by means of the nanometer dimensions of the coating particles. Briefly, when nanometer dimensions are reached, the optical, magnetic and electrical properties of matter change radically. By reducing the dimensions until the typical nanometer dimensions of so-called clusters are reached, due to the small number of atoms that are present in said cluster and to its reduced volume, a discretization of the energy levels (quantization) becomes apparent in the electron structure and depends on the size of the cluster, this phenomenon is known as "quantum size effect", and entirely new characteristics, which contrast with the ones that are typical of the material at ordinary dimensions, depend from it.

In the present case, the best performance has been obtained with powders which have a size distribution centered in an interval ranging from 60 to 80 nm as indicated above.

As a whole, the effects described above produce the simultaneous presence of three factors which are a key aspect of the invention: stability of the resulting acid water, ease of its production (for example thanks to the lower maintenance costs and to the greater durability of the device as a whole) and an increase in its quality (especially in terms of purity and constancy of properties over time). In particular, the increase in the quality of the acid water can be measured both in terms of uniformity of the dimensions of the molecular clusters (higher percentage of micromolecules with respect to the number of macromolecular clusters) and in terms of increased stability over time of the properties given to the water by the electrolysis itself (above all acidity, ORP and cluster size). The stability increase presumably achieves the preservation over time of the structural surface characteristics of the electrodes coated with a nanocoating as described here.

In another aspect, the present invention relates to a device 1 particularly for the electrolytic treatment of water, which comprises at least one chamber 7 and 8 for treating said water and at least one pair of electrodes 3 and 4 for each chamber, said electrodes 3 and 4 being arranged within said at least one chamber 7 and 8, wherein the device 1 is characterized in that at least one of the electrodes 3 or 4 that are present is as defined above.

The embodiment in which the device 1 comprises a single electrolysis chamber 7 and 8 and a single pair of electrodes 3 and 4 within said chamber 7 and 8 is described hereinafter. However, the person skilled in the art will know how to adapt the description to other embodiments which comprise more than one electrolysis chamber and more than one pair of the electrodes. The number of chambers can be changed, for example, in order to achieve higher treatment speeds or flow-rates of water in output.

In a highly preferred embodiment, both electrodes 3 and 4 of the device are electrodes as defined above. However, the advantages in terms of low cost and efficiency of the electrolysis process, as well as the advantages in terms of stability over time of acid and basic water, can be obtained also if only one of the two electrodes is as defined above.

Preferably, the device according to the invention also comprises a membrane 6, which is adapted to divide the at least one chamber into two half-chambers 7 and 8, each half-chamber containing one of the two electrodes 3 or 4, wherein the half-chamber 8 that contains the anode 4 is termed anode half-chamber, while the half-chamber 7 that contains the cathode 3 is termed cathode half-chamber. The membrane 6 is advantageously an ultrafiltration membrane which can occupy the chamber partially or totally.

The membrane 6 can be of the type used in conventional electrolytic cells. However, in a particularly advantageous embodiment the membrane is made of ceramic material with open porosity, coated with metallic nanoparticles, preferably nanoparticles of oxide of zirconium, yttrium, aluminum or mixtures thereof.

By resorting to nanometer particles to manufacture the membrane 6, the average pore size of the final membrane has been found to be extremely constant over time and adaptable according to the requirements of how the water is to be processed.

Size constancy over time and constancy of the pore dimensions themselves are two aspects which differentiate the ceramic membrane 6 described here from the textile membranes conventionally used in equivalent devices (which are instead subject to rapid deterioration over time). These aspects have shown a positive effect on the stability of the liquid fractions (acid and basic water) obtained after electrolysis, where this effect combines with, and augments, the stabilizing effect produced by the use of an electrode as defined above.

In a particularly advantageous embodiment, each half-chamber 7 and 8 is connected to the outside of the device 1 through:
- an opening (not designated by a reference number in the figures) arranged in the upper part of the half-chamber 7 or 8 from which the water to be subjected to electrolysis is inserted, and through
- an additional opening 10 and 11, which is arranged in the lower part of the half-chamber 7 or 8 which can act as a discharge for the resulting acid and basic fractions. The second opening 10 and 11 is provided with closure means (not shown) which are adapted to prevent the water that has not yet separated from leaving the half-chamber and are adapted to be opened at the end of the electrolysis process.

With specific reference to FIG. 1, the operating mechanism of a device 1 as described above, provided with all the essential and optional elements that have been listed, therefore entails treating water by introducing it from above, by means of the duct 9, into the two half-chambers 7 and 8 of the chamber 2. Here, the water, under the action of the cathode 4 and of the anode 3 previously connected to the negative and positive poles of an electric voltage source, is split into positive and negative ions, which, as is known, are attracted to the respective opposite poles. In passing from one half-chamber to the other, the nanoporous membrane 6 acts as a filter for said ions and for any charged particles, allowing only the particles of sufficiently small size to pass.

In another aspect, the present invention relates to an apparatus particularly for the electrolytic treatment of water which is characterized in that it comprises a device 1 as defined above.

In one embodiment of the invention, the apparatus comprises means 12 for pretreating the water, means for the electrolytic treatment of water, arranged downstream of said pretreatment means, and a hydraulic circuit for connecting said pretreatment means to said treatment means, wherein said electrolytic treatment means comprise a device 1 as defined above.

The expression "pretreatment means" references means which are adapted to treat the water before subjecting it to electrolysis. Pretreatment means can comprise one or more elements selected among:
- one or more batteries of filters 14,
- one or more units 15 for magnetizing the water, and
- one or more units 16 for adding one or more optional ingredients to the water.

In particular, the battery of filters 14 can comprise one or more prefilters 17, one or more microporous filters 18, and one or more activated-carbon filters 19, so as to suppress physically any solid fraction that is present in suspension. The three types of filter suppress solids with respect to a decreasing size. Accordingly, if they are present simultaneously, in order to be effective they must be used in the order in which they are presented here.

In a per se known manner, the magnetizing unit 15 is useful to separate from the water any traces of suspended metals.

In the unit 16 for adding additives to the fluid it is possible to combine the fluid with ingredients, such as salts, for example sodium chloride, which will act as a carrier for subsequent electrolysis.

In one embodiment it is possible to arrange additional filters 20 between the magnetizing unit (downstream thereof) and the additive addition unit (upstream thereof) or directly upstream of the electrolysis device 1.

In another aspect, the invention relates to a method for performing the electrolysis of water, wherein said method comprises a step a) of subjecting to electrolysis a given amount of water inside a device as defined above.

In one embodiment of the invention, the method comprises an additional step a1) of pretreating the water before subjecting it to step a), by means of one or more filtration, magnetization and additive addition steps. The filtration step is important, because any solids suspended in the water would be harmful for electrolysis and would rapidly reduce the average life of the electrodes and the membrane of said device.

In one embodiment of the invention, the method comprises an additional step b), which follows the step a), for separating the components of acid and basic water generated by electrolysis.

The term "filtration" is used to reference the removal from water of suspended solids. Filtration can occur by way of known means, such as one or more prefilters, one or more microporous filters and one or more activated-carbon filters, so as to suppress physically the suspended solid.

The term "magnetization" is used to reference the application of a magnetic field to the water in order to remove any traces of metals present therein, which, if not removed, might eliminate rapidly the particular properties (for example ORP, pH and size of the molecular cluster) given to the anode and cathode fractions by the electrolysis process.

The expression "additive addition" is used to reference the addition to the water of one or more optional ingredients, such as for example salts, which are known to possibly have a positive effect in terms of the speed of the subsequent electrolysis step a).

In another aspect, the present invention relates to an electrolytic acid water, particularly as a sanitizing agent, which can be obtained with a water electrolysis method as defined above.

The electrolytic acid water according to the present invention differs from known similar products substantially in its stability, which is due presumably to the absence of heavy metals. Even by subjecting the water to a filtration step before treating it with conventional electrolysis, the electrodes that are currently used for electrolysis in fact tend to break up on their surface during the process, releasing large amounts of heavy metals (particularly of the metal or metals of which the cathode is made).

The acid water according to the invention is instead free from heavy metals in that said metals, if present, are present in a quantity which is below the limits that can be detected with ordinary analytical methods. For example, the acid water according to the invention has a cadmium concentration of less than 5 μg/l, less than 10 μg/l of chromium, less than 5 μg/l of lead, and less than 20 μg/l of nickel.

Although one does not intend to be bound to any particular theory, it is believed that the absence of heavy metals is the main reason for the unusual and advantageous stability over time of the electrolytic acid water obtained with the present invention. The expression "stability over time" is used to mean that the acid water of the present invention, if kept sheltered from the light, air and heat, keeps its chemical and physical properties, particularly its pH, ORP and molecular cluster size, unchanged for up to 90 days, preferably up to 180 days, even more preferably up to 365 days.

Although the stability time depends on the preservation characteristics, it must be noted that for equal storage conditions, an acid water obtained by using an electrolytic device as defined above has shown a distinctly higher stability than known similar products, which in the best cases have shown a shelf life of only 15-30 days. Therefore, these products must be obtained and used over a short period or even simultaneously with their production. Therefore, the electrolytic acid water according to the invention can be used usefully also for applications in locations (Third World countries) and situations (scarcity of water to provide electrolysis) in which, although it is necessary to have for example a valid disinfectant, favorable conditions for its production are not available.

In a preferred embodiment, the electrolytic acid water according to the invention is free from heavy metals, has a pH which is advantageously equal to, or lower than, 3.0 but higher than 0, preferably ranging from 1.5 to 3.0, an ORP (oxide reduction potential) equal to, or greater than, 1000 mV, preferably from 1000 mV to 1300 mV, more preferably approximately equal to 1150 mV, and a molecular cluster of 10 or less but more than 0, preferably equal to 5.

The expression "molecular cluster" designates the number of molecules of water which are coordinated in an ordered structure. Nuclear magnetic resonance $^{17}O$ NMR (a parameter which is adopted universally to measure the size of clusters) shows that the amplitude halfway along the peak of an anode water according to the invention is 51-52 Hz, while for known products it is 110-130 Hz. These values indicate that the clusters of an anode water according to the invention have an extremely constant size and comprise a low number of water molecules, preferably less than 10, more preferably approximately 5. Conventional acid waters instead contain clusters of variable size which contain up to a few tens of water molecules which are mutually coordinated. The reduced size of the molecular clusters gives the anode water according to the invention particular properties, such as improved solvent capacity, higher penetration power and faster osmosis.

In one embodiment, the acid water according to the invention comprises active chlorine, which is generated during the electrolytic process, at an average concentration of less than 60 mg/l. In this manner, the aqueous solution according to the invention has an extremely low toxicity for humans and substantially no environmental impact. In other words, a specific advantage of the anode water according to the invention is that after it has been applied in the chosen manner the residues that are left are rapidly converted by the combined action of light and oxygen into compounds which are harmless to humans and to the environment, such as ordinary water and sodium chloride.

It should also be noted that the fixed residue of an electrolytic acid water is distinctly lower than the fixed residue of any other differently obtained disinfectant composition. Therefore, thanks to its stability, the anode water according to the invention can be used for example in all those sectors, such as cleaning and maintaining the hygiene of contact lenses, in which one wishes to combine a high but prolonged disinfectant power with the need to not leave deposits or residues on the treated surfaces. Currently, the use of electrolytic acid waters for this purpose is prevented by the limited stability over time of the disinfectant power.

In another aspect, the present invention relates to a composition particularly for sanitizing a substrate which comprises an acid water as defined above and one or more ingredients selected from the group that comprises:

i) excipients and carriers which are pharmaceutically acceptable for preparing pharmaceutical compositions for human or animal use, ii) excipients and carriers which are cosmetically acceptable for preparing cosmetic compositions for human or animal use, iii) excipients and carriers used to prepare disinfectant compositions, and iv) excipients and carriers used in the agricultural sector to prepare antiparasitic or fungicide compositions.

The terms "sanitize", "sanitization" or "sanitizing" in the invention reference the provision of a combined effect of disinfection, sanitization and cleaning. In particular, the disinfection effect comprises a bactericidal, fungicide, sporicidal and virucidal effect.

Preferred pharmaceutically acceptable excipients and carriers are excipients and carriers usually used to prepare topical disinfectant compositions or to prepare skin treatment compositions. Examples are polymers of vegetable origin (derivatives of cellulose or starch) or synthetic ones (acrylic polymers) or animal-derived polymers (collagen).

The expression "excipients and carriers used for disinfectant compositions" is used to reference ingredients which are commonly used to prepare:

disinfectant compositions for edible products (food sector), disinfectant compositions for environments, devices and medical-surgical instruments, disinfectant compositions for human or animal reimplantation tissues, disinfectant compositions for cleaning and maintaining the hygiene of contact lenses and optical material in general, disinfectant compositions for home surfaces and environments.

In another aspect, the present invention relates to a kit which comprises an electrolytic acid water as defined above or a composition which comprises said water and means for applying it to a substrate.

The substrate is advantageously selected among 1) inanimate objects and surfaces, 2) the human or animal body, and 3) isolated parts of the human or animal body. Examples of the three classes mentioned above are provided below with reference to the aspect of the sanitizing use of an acid water as defined above.

Some applications of an acid water according to the invention are described hereinafter and are allowed by the particular properties thereof and especially by the combination now obtainable of easy production at very low costs, stability of the resulting water and purity thereof.

In another aspect, the present invention relates to the use of an electrolytic acid water as defined above or of a composition which comprises it to prepare a medication for treating and preventing superficial or deep skin disorders or lesions of the human or animal body.

The use to prepare a medication, exactly like all of the aspects of use discussed below, is described with explicit reference to the use of an acid water according to the invention. However, it will be immediately evident to the person skilled in the art that the same advantages in terms of use can be achieved by using not the acid water per se but a composition as defined above which comprises it.

The expression "treatment or prevention" means that thanks to its properties, mainly pH and ORP, an electrolytic acid water according to the invention or a composition which comprises it have been found to be effective for the treatment and remission of surface or deep skin pathologies or lesions that are already occurring (for example healing of injuries or lesions of the skin or dermis, control and remission of bacterial, mycotic or viral infections affecting the skin or dermis), or to reduce the risk of developing deep or superficial pathologies or lesions of the skin.

It is also understood that the treatment effects and prevention also apply to disorders which are systemic but in which the etiogenesis can be ascribed to the cutaneous penetration of infectious agents. Early treatment of the skin infection in fact allows to eliminate the infectious agent before it achieves systemic diffusion.

The expression "surface or deep skin lesions or pathologies" references preferably:
  cutaneous phenomena associated with allergic, inflammatory and immunological reactions, such as irritations and erythemas, affecting the epidermis and/or dermis. Examples of irritations are nettle rashes, dermatitides (allergic or contact-related), eczemas, psoriases, vitiligos and dandruff. For treatment of psoriasis, the effectiveness of the acid water according to the invention is probably due to the exfoliating effect of the active chlorine contained therein;
  superficial or deep cutaneous phenomena caused by bacterial and/or mycotic and/or viral infections, and
  lesions or abrasions of the skin and/or dermis, such as burns, sunburns and bedsores.

The broad-spectrum biocidal functions exhibited by the electrolytic acid water of the invention and by the compositions that comprise it are confirmed not only by the results of the tests on specific pathogens but also by the fact that the product according to the present invention is capable of degrading completely the nucleic acids of pathogens.

As mentioned, the acid water according to the invention can be used for the treatment and remission of burns or sunburns of the skin or for the healing of wounds, by virtue of its low toxicity and high penetration capacity. One aspect which demonstrates the high penetration capacity of the acid water described here is its high swelling power seen on tissues which are dehydrated and preserved in appropriate banks while waiting for transplants in humans or animals (reimplantation tissues).

Moreover, the aqueous solution according to the invention, in view of its broad range of action against microorganisms or viruses, can be used for example to eliminate parasitoses of viral and/or bacterial origin of plants intended for food use (for example fruits, leafy vegetables, et cetera) or for domestic/decorative use (apartment plants, flowers).

In another aspect, the present invention relates to the use of an electrolytic acid water as defined above or to a composition which comprises it to sanitize a substrate.

Advantageously the substrate is selected among 1) inanimate objects and surfaces, 2) surfaces of the human or animal body, and 3) surfaces of isolated parts of a human or animal body.

Preferred inanimate surfaces and objects are domestic spaces and objects, medical and medical-surgical devices and instruments (for example teats, endoscopes or other medical tools), contact lenses and optical instruments in general, surfaces of edible products, for example fruits or vegetables.

Preferred surfaces of the human or animal body are parts of a patient or surgeon before or after surgery, and human breasts or animal udders.

Preferred surfaces of isolated parts of the human or animal body are human or animal reimplantation tissues, such as tendons, wherein said tissues can be dehydrated or not.

In a further aspect, the present invention relates to the use of an electrolytic acid water as defined above or of a composition which comprises it for cosmetic treatment of the human or animal body or of isolated parts thereof.

Cosmetic use relates in particular to the treatment of the skin, particularly the skin of areas of the human body which are subject to rashes, such as the skin of hands, feet and face. The acid pH of the product, by restoring ordinary skin acidity, which is altered in reddening and inflammatory situations, in fact allows faster recovery of skin functionality.

Moreover, the acid water according to the invention has exhibited a surprising capacity to dissolve the cutaneous lipid secretion, so that it can be used in the cosmetic treatment of acne and blackheads.

Also in the cosmetic field, importance is given to the property exhibited by the acid water according to the invention to dissolve most of the chemical residues left by the application of cosmetics to the skin and already partially absorbed by the surface layers of said skin, and to the capacity to remove from the skin the fine powders which are generated by pollution and are adsorbed thereon.

In another aspect, the present invention relates to the use of an electrolytic acid water as defined above or to a composition which comprises it to carry preparations suitable for bone reconstruction.

The solutions for bone reconstruction must be acid, since they generally contain collagen, which however, in order to be carried, must be first dissolved and made to gel (effects which can be obtained only in an acid environment). The acid water obtained with the invention is an improvement of current collagen carriers for bone reconstruction, since in addition to ensuring the acidity needed to dissolve the collagen and make it gel, it also has a conspicuous and durable bactericidal, virucidal and antimycotic power, which is highly advantageous for medical-surgical applications which have a high risk of infection.

In another aspect, the present invention relates to the use of an electrolytic acid water as defined above or of a composition which comprises it to rehydrate human or animal dehydrated tissues for reimplantation (see in this regard the figure of example 7).

Tissues for human or animal reimplantation are preserved, after being explanted from the donor and while waiting for reimplantation, in appropriately provided sterile banks, usually after dehydration (for example by freeze drying), so as to slow and prevent the growth of bacteria. When the acid water according to the invention has been used to rehydrate the tissues before reimplantation, a drastic reduction of rehydration times has been observed with respect to the aqueous solutions conventionally used for this purpose. The rehydration effect may be due to the high ability to dissolve the keratin components of tissues exhibited by the acid water according to the invention and to its substantial penetration power, which determines a so-called "moisture retaining" effect on the part of the tissues. The application described above was unthinkable for conventional acid waters due to their low purity (especially in terms of heavy metals) and low stability.

From what has been described above it is evident that the invention achieves the intended aim and objects, and in particular the aim of providing an electrolytic acid aqueous solution having characteristics which are already known but a much higher stability than conventional products.

The invention is susceptible of numerous modifications and variations, all of which are within the scope of the inventive concept expressed in the appended claims. All the details may be replaced with other technically equivalent elements and the materials may be different according to requirements without abandoning the scope of the invention.

Other characteristics and advantages of the present invention will become better apparent from the description of the following preferred embodiments, intended exclusively by way of non-limiting example.

Tables which contain data regarding the effectiveness of an electrolytic acid water obtained with a device according to the invention, used in the context of the applications described above, are presented hereafter.

The sample of water used in all the tests that follow is referenced as "solution 259" and was taken from an amount of acid water having a pH of approximately 2.69, an ORP of approximately 1135 mV, and a cluster size of approximately 5.

EXAMPLE 1

The concentration of heavy metals in this sample was verified by a certified laboratory at the Applicant's request. The data are provided hereafter.

| TEST REPORT NO. 30572/2005 Sample of SOLUTION 259 | |
|---|---|
| References | BATCH 0510001 ORP 1138 |
| Analysis start date | 18 Oct. 2005 |
| Analysis end date | 25 Oct. 2005 |
| Arrival temp. | +4° C. |
| State of preservation | GOOD |
| Collected by | YOUR STAFF |
| Collected on | 14 Oct. 2005 |
| Received on | 14 Oct. 2005 |
| Package | PET BOTTLE |
| Collection temp. | N/D |

| RESULTS OF TESTS | | | |
|---|---|---|---|
| Test | Testing method | U.M. | Value |
| CADMIUM | APAT CNR IRSA 3120/2003 | µg/l | <5 |
| TOTAL CHROMIUM | APAT CNR IRSA 3150/2003 | µg/l | <10 |
| LEAD | APAT CNR IRSA 3230/2003 | µg/l | <5 |
| NICKEL | APAT CNR IRSA 3220/2003 | µg/l | <20 |
| FIXED RESIDUE AT 180° C. | APAT CNR IRSA 2090A/2003 | mg/l | 3.198 |

It is therefore clearly evident that the acid water 259 has no heavy metals and is therefore pure and therefore stable.

EXAMPLE 2

The sample of water 259 was then subjected to a test in order to assess its transdermal absorption on mouse skin, calculating as parameters linked to transdermal absorption the osmotic concentration and cumulative penetration in comparison with a control sample (and a blank).
Effect of Increased Penetration:
Methods and materials: tested sample: solution 259, colorless and transparent liquid, mixed at 5% with vitamin E,
Control sample: conventional latex with 5% vitamin E.
Testing instrument: UV-2100 for ultraviolet spectrophotometry (SHIMADZU Japan)
Tested animals: mouse (Kunming species)
Quantity: 2 (males:females=50:50)
Weight: 18-22 g
Temperature: 16-21° C.
Relative humidity: 40-60%
Experimental method: the animals were kept without food for up to 16 hours; fur was removed from the back by chemical hair removal (8% $Na_2S$ alcohol solution); the hairless skin was fixed and isolated; the skin was removed after washing; the subcutaneous and adipose tissue and mucosae were collected; the undamaged part was cut; preservation in a refrigerator after rinsing with saline solution was performed.
Sample preparation: solution 259 was diluted with glycerin, producing multiple dilutions thereof respectively by 1, 2, 4, 5 and 10 times, identified with the codes S-1, S-2, S-4, S-5, S-10.
Dilution of the control with glycerin with multiple dilution for 1 time.
Results:

| Osmolarity of solution 259 on isolated mouse skin (µg/ml, n = 9) | | | | | |
|---|---|---|---|---|---|
| | Sampling time (h) | | | | |
| Sample | 0.167 | 0.5 | 1 | 1.5 | 2.5 |
| S-1 | 6.274** | 6.706** | 8.362** | 8.772** | 10.234** |
| S-2 | 5.986** | 7.282** | 8.434** | 9.658** | 9.226** |
| S-4 | 5.498** | 8.434*** | 9.010** | 9.514** | 10.666*** |
| S-5 | 5.626** | 6.346** | 7.714** | 8.218** | 8.65** |
| S-10 | 4.906* | 5.338** | 5.986 | 6.994* | 7.210* |
| Blank | 0 | 0.658* | 0.946* | 1.090* | 1.234* |
| Contr. | 2.458 | 2.530 | 3.250 | 3.898 | 5.194 |

| | Sampling time (h) | | | |
|---|---|---|---|---|
| Sample | 4 | 6 | 8 | 10 |
| S-1 | 11.530* | 13.690* | 16.030* | 14.698* |
| S-2 | 11.026* | 11.386 | 11.890* | 13.690* |
| S-4 | 11.674* | 12.358 | 12.687 | 15.346 |

-continued

Osmolarity of solution 259 on isolated mouse skin (μg/ml, n = 9)

| S-5 | 9.370 | 11.026 | 12.178 | 11.674** |
| S-10 | 7.210* | 8.002* | 8.434** | 9.514*** |
| Blank | 1.882* | 1.809* | 3.034*** | 3.133*** |
| Contr. | 9.802 | 10.666 | 14.338 | 17.794 | where Contr. = control, and with respect to the sample,
*P < 0.05,
**P < 0.01,
***P < 0.001.

Cumulative penetration of solution 259 on isolated mouse skin (μg/ml, n = 9)

| | Sampling time (h) | | | | |
| --- | --- | --- | --- | --- | --- |
| Sample | 0.167 | 0.5 | 1 | 1.5 | 2.5 |
| S-1 | 6.274 | 7.020** | 8.697** | 9.140** | 10.670** |
| S-2 | 5.986 | 7.581** | 8.798** | 10.079*** | 9.710** |
| S-4 | 5.498 | 8.709*** | 9.432** | 9.965*** | 11.162*** |
| S-5 | 5.626 | 6.627** | 8.031** | 8.604** | 9.061** |
| S-10 | 4.906 | 5.583** | 6.253** | 7.293* | 7.560 |
| Blank | 0 | 0.658* | 0.979* | 1.137* | 1.289* |
| Contr. | 2.458 | 2.682 | 3.376 | 4.060 | 5.389 |

| | Sampling time (h) | | | |
| --- | --- | --- | --- | --- |
| Sample | 4 | 6 | 8 | 10 |
| S-1 | 12.042* | 14.267* | 16.715 | 15.500 |
| S-2 | 11.487 | 11.937 | 12.459 | 14.285* |
| S-4 | 12.207 | 13.122 | 13.309 | 15.980 |
| S-5 | 9.802 | 11.495 | 12.729 | 12.283* |

-continued

Cumulative penetration of solution 259 on isolated mouse skin (μg/ml, n = 9)

| S-10 | 7.571* | 8.363* | 8.834** | 9.936** |
| Blank | 1.944*** | 1.904*** | 3.125*** | 3.258*** |
| Contr. | 10.062 | 11.156 | 14.871 | 18.510 | where Contr. = control, and with respect to the sample,
*P < 0.05,
**P < 0.01,
***P < 0.001.

Cumulative penetration can be identified 10 minutes (0.167 hours) after applying diluted solution 259 to the horny layer and becomes stable after approximately 4 hours. Cumulative penetration of the control sample, calculated after approximately 1.5 hours, exhibited an extent approximately 55.8% lower than that of solution 259. A significant difference in P between solution 259 and the control was also observed.

EXAMPLE 3

The toxicity of solution 259 is calculated, assessing for this purpose its acute dermal irritation and eye irritation.

Dermal irritation: protocol adopted in accordance with article 3.6 of 1999.11 volume 1 (experimental criteria), version 3 (sterilization technology criteria) issued by the Chinese Health Ministry.

Methods and materials: tested sample: unmixed solution 259, colorless and transparent liquid, Tested animals: rabbit (New Zealand species)

Quantity: 4 (males:females=50:50)

Weight: 2.5-3.0 kg, provided by the University of Fudan, experimental animal division, certificate number 02-52-1

Temperature: 18-22° C.

Relative humidity: 40-70%

Experimental method: fur was removed from regions measuring 3×3 cm on both sides of the spinal column of the animals 24 hours before the experiment. After 24 hours, 0.2 ml of solution 259 were applied to the left side; the test region was then covered with transparent paper and fixed with a nonirritating elastic bandage. The right region was used as comparison. After 1, 24 and 48 hours, the bandage was removed, the remaining solution 259 was washed, the degree of irritation was determined and a classification was performed (0=absent, 1=present), of extent of edema (E), erythema (R), and total irritation (T).

Results:

| | | | 1 h | | | | | | 24 h | | | | | | 48 h | | | | |
| --- | --- | --- | --- | --- | --- | --- | --- | --- | --- | --- | --- | --- | --- | --- | --- | --- | --- | --- | --- |
| | | | L | | | R | | | L | | | R | | | L | | | R | |
| Anim. | Sex | Wt | E | R | T | E | R | T | E | R | T | E | R | T | E | R | T | E | R | T |
| 1 | F | 3.0 | 0 | 0 | 0 | 0 | 0 | 0 | 0 | 0 | 0 | 0 | 0 | 0 | 0 | 0 | 0 | 0 | 0 | 0 |
| 2 | M | 2.5 | 0 | 0 | 0 | 0 | 0 | 0 | 0 | 0 | 0 | 0 | 0 | 0 | 0 | 0 | 0 | 0 | 0 | 0 |
| 3 | F | 2.6 | 0 | 0 | 0 | 0 | 0 | 0 | 0 | 0 | 0 | 0 | 0 | 0 | 0 | 0 | 0 | 0 | 0 | 0 |
| 4 | M | 2.7 | 0 | 0 | 0 | 0 | 0 | 0 | 0 | 0 | 0 | 0 | 0 | 0 | 0 | 0 | 0 | 0 | 0 | 0 |

As is evident, in no case any acute irritation phenomenon at the dermal level occurred.

Eye irritation: protocol adopted in accordance with article 3.7 of 1999.11 volume 1 (experimental criteria), version 3 (sterilization technology criteria) issued by the Chinese Health Ministry.

Methods and materials: tested sample: unmixed solution 259, colorless and transparent liquid, Tested animals: rabbit (New Zealand species)

Quantity: 4 (males:females=50:50)

Weight: 2.5-3.0 kg, provided by the University of Fudan, experimental animal division, certificate number 02-52-1

Temperature: 18-22° C.

Relative humidity: 40-70%

Experimental method: the left eyelid of the tested animals was gently parted, 2 drops of solution 259 were dropped into the conjunctiva, an equal amount of physiological solution was dropped into the right eye. 1, 24, 48, 72 hours and 4 and 7 days after application, the eye was washed with saline solution for 5 minutes, then, after closing the eyelids for 4 seconds, the damage was observed; the cornea, iris and conjunctiva were recovered from the two exposed eyes and washing with 2% sodium fluorescein was performed. Finally, the degree of acute eye irritation was evaluated, a scale of points was defined and a degree was given to the average total eye irritation (T), to cornea irritation (C), iris irritation (I), and conjunctiva irritation (O).

Results:

| | | Degree of eye irritation reaction | | | | | | | | | | |
|---|---|---|---|---|---|---|---|---|---|---|---|---|
| | | 1 | | 24 | | 48 | | 72 | | 4th day | | 7th day |
| Anim. | Area | L | R | L | R | L | R | L | R | L | R | L | R |
| 1 | C | 0 | 0 | 0 | 0 | 0 | 0 | 0 | 0 | 0 | 0 | 0 | 0 |
| | I | 0 | 0 | 0 | 0 | 0 | 0 | 0 | 0 | 0 | 0 | 0 | 0 |
| | O | 0 | 0 | 0 | 0 | 0 | 0 | 0 | 0 | 0 | 0 | 0 | 0 |
| | T | 0 | 0 | 0 | 0 | 0 | 0 | 0 | 0 | 0 | 0 | 0 | 0 |
| 2 | C | 0 | 0 | 0 | 0 | 0 | 0 | 0 | 0 | 0 | 0 | 0 | 0 |
| | I | 0 | 0 | 0 | 0 | 0 | 0 | 0 | 0 | 0 | 0 | 0 | 0 |
| | O | 0 | 0 | 0 | 0 | 0 | 0 | 0 | 0 | 0 | 0 | 0 | 0 |
| | T | 0 | 0 | 0 | 0 | 0 | 0 | 0 | 0 | 0 | 0 | 0 | 0 |
| 3 | C | 0 | 0 | 0 | 0 | 0 | 0 | 0 | 0 | 0 | 0 | 0 | 0 |
| | I | 0 | 0 | 0 | 0 | 0 | 0 | 0 | 0 | 0 | 0 | 0 | 0 |
| | O | 0 | 0 | 0 | 0 | 0 | 0 | 0 | 0 | 0 | 0 | 0 | 0 |
| | T | 0 | 0 | 0 | 0 | 0 | 0 | 0 | 0 | 0 | 0 | 0 | 0 |
| 4 | C | 0 | 0 | 0 | 0 | 0 | 0 | 0 | 0 | 0 | 0 | 0 | 0 |
| | I | 0 | 0 | 0 | 0 | 0 | 0 | 0 | 0 | 0 | 0 | 0 | 0 |
| | O | 0 | 0 | 0 | 0 | 0 | 0 | 0 | 0 | 0 | 0 | 0 | 0 |
| | T | 0 | 0 | 0 | 0 | 0 | 0 | 0 | 0 | 0 | 0 | 0 | 0 |

As can be seen, solution 259 must be classified as nonirritant for the mucosae of the eye.

EXAMPLE 4

The regenerating property of solution 259 is tested.

Testing method: 78 patients were involved, divided into two groups: A, 35 patients with surface burns; and B, 43 patients with deep burns. 25 patients of group A (S-1) and 31 patients of group B (S-2) were treated with sulfadiazine after being treated with solution 259 for debridement. The remaining 10 patients of A (control-1) and 12 of B (control-2) were treated with sulfadiazine after being treated conventionally for debridement.

Results:

| Group | Number of patients | Days for healing (X ± SD dd) |
|---|---|---|
| S-1 | 25 | 10.1 ± 3.2* |
| Control-1 | 10 | 14.5 ± 3.8 |
| S-2 | 31 | 19.2 ± 2.6* |
| Control-2 | 12 | 23.6 ± 3.1 |

With *P < 0.01.

Treatment with solution 259 produced a faster regrowth of the epidermis and fibroblasts on the burned areas, did not cause irritation, suppressed tissue edema, reduced surface infection, kept the wounds relatively dry and conspicuously reduced healing times.

EXAMPLE 5

The bactericidal power of solution 259 was tested by a certified laboratory at the Applicant's request. The data are presented in the table that follows. The experimental details are also provided.

Testing Method and Validation Thereof:

Method: dilution-neutralization;

Neutralizing agent: 30 g/l of polysorbate 80 (Tween® 80)

Experimental Conditions:

Diluent of the product used during the test: hard water (300 mg/kg of $CaCO_3$), sterile.

Test concentrations of the product: 100%; 80% (V/V).

Appearance of the dilutions of the product: clear and colorless solution.

Contact time: t=5 min±10 s.

Test temperature: $\theta$=20° C.±1° C.

Interfering substance: 0.3 g/l of bovine albumin for simulating clean conditions; 3 g/l of bovine albumin for simulating dirty conditions.

Stability of the mixture (interfering substance and test product, diluted and as is): precipitate is absent throughout the test.

Incubation temperature: 37° C.±1° C.

Identification of the bacterial strains used: *Pseudomonas aeruginosa* ATCC 10145; *Escherichia coli* ATCC 11775; *Staphylococcus aureus* ATCC 29213; *Enterococcus hirae* ATCC 8043.

| | Validation test | | | |
|---|---|---|---|---|
| Organism | Bacterial suspension | Experimental conditions | Neutralizing toxicity control | Dilution-neutralization control |
| *Pseud. aeruginosa* ATCC 10145 | $N_v =$ $8.2 \times 10^2$ | A = $3.4 \times 10^2$ | B = $2.3 \times 10^2$ | C = $2.8 \times 10^2$ |
| *Esch. coli* ATCC 11775 | $N_v =$ $1.4 \times 10^3$ | A = $6.1 \times 10^2$ | B = $5.6 \times 10^2$ | C = $6.2 \times 10^2$ |
| *Staph. aureus* ATCC 29213 | $N_v =$ $2.8 \times 10^3$ | A = $9.6 \times 10^2$ | B = $9.2 \times 10^2$ | C = $9.4 \times 10^2$ |
| *Enter. hirae* ATCC 8043 | $N_v =$ $1.3 \times 10^3$ | A = $8.0 \times 10^2$ | B = $7.2 \times 10^2$ | C = $8.2 \times 10^2$ |

| | | Test method at the concentration % (V/V) | | | |
|---|---|---|---|---|---|
| | | 100 | | 80 | |
| Organism | Bacterial test suspension | Clean conditions (0.3 g/l bovine albumin) | Dirty conditions (3 g/l bovine albumin) | Clean conditions (0.3 g/l bovine albumin) | Dirty conditions (3 g/l bovine albumin) |
| *Pseud. aeruginosa* ATCC 10145 | N = $1.7 \times 10^8$ | $N_a = 0$ R = >$10^8$ | $N_a = 1$ R = $10^8$ | $N_a = 0$ R = >$10^8$ | $N_a = 2.7 \times 10^4$ R = $10^4$ |

-continued

| | | Test method at the concentration % (V/V) | | | |
| | | 100 | | 80 | |
| Organism | Bacterial test suspension | Clean conditions (0.3 g/l bovine albumin) | Dirty conditions (3 g/l bovine albumin) | Clean conditions (0.3 g/l bovine albumin) | Dirty conditions (3 g/l bovine albumin) |
|---|---|---|---|---|---|
| Esch. coli ATCC 11775 | $N = 5.0 \times 10^8$ | $N_a = 0$<br>$R = >10^8$ | $N_a = 25$<br>$R = 10^8$ | $N_a = 0$<br>$R = >10^8$ | $N_a = 1.4 \times 10^4$<br>$R = 10^4$ |
| Staph. aureus ATCC 29213 | $N = 4.9 \times 10^8$ | $N_a = 0$<br>$R = >10^8$ | $N_a = 5.4 \times 10^6$<br>$R = 10^2$ | $N_a = 0$<br>$R = >10^8$ | $N_a = 8.2 \times 10^7$<br>$R = 10$ |
| Enter. hirae ATCC 8043 | $N = 4.8 \times 10^8$ | $N_a = 1$<br>$R = 10^8$ | $N_a = 4.2 \times 10^6$<br>$R = 10^2$ | $N_a = 1$<br>$R = 10^8$ | $N_a = 7.8 \times 10^6$<br>$R = 10^2$ | where: Nv=number of CFU/ml of the bacterial suspension used for the validation tests; A=number of CFU/ml in the validation of the experimental conditions; B=number of CFU/ml in the validation of the toxicity of the neutralizing agent; C=number of CFU/ml in the validation of the dilution-neutralization; N=number of CFU/ml of the test bacterial suspension; Na=number of CFU/ml in the test mix; R=extent of the reduction of the microbial burden.

The data contained in the table confirm that according to the UNI EN 1276:2000 standard, batch L 0510001 with an ORP of 1138 of the product "solution 259" has a bactericidal activity in 5 minutes at 20° C. for the reference strains Pseudomonas aeruginosa ATCC 10145, Escherichia coli ATCC 11775, Staphylococcus aureus ATCC 29213, Enterococcus hirae ATCC 8043, both when the product is used at 100% (V/V) and when it is used after dilution in hard water at 80% (V/V), in "clean" conditions (0.3 g/l of bovine albumin). As expected, in "dirty" conditions (3.0 g/l of bovine albumin), the product has a lower bactericidal activity.

EXAMPLE 6

The virucidal power of solution 259 was tested directly by the Applicant in its own laboratories. The data are given in the table that follows.

| | | Infection number (TCID 50/ml) | |
| | S/N (60 s after processing) | Before processing | 30 s after processing |
|---|---|---|---|
| HIV-1 | | $10^{4.5}$ | 0 |
| Poliovirus-1, -2, -3 | | $10^{5.2}$ | 0 |
| HBsAg | 0.97 | | |
| Cytomegalovirus | | $10^{5.2}$ | 0 |
| HSV-1 | | $10^{5.3}$ | 0 |
| HSV-2 | | $10^{5.8}$ | 0 | where: S=OD of the sample group and N=OD of the negative group, S/N<2.1=broken antigen HBsAg; ORP of acid water=from 1152 to 1180 mV; pH of acid water=from 2.35 to 2.6.

EXAMPLE 7

Figure 3:
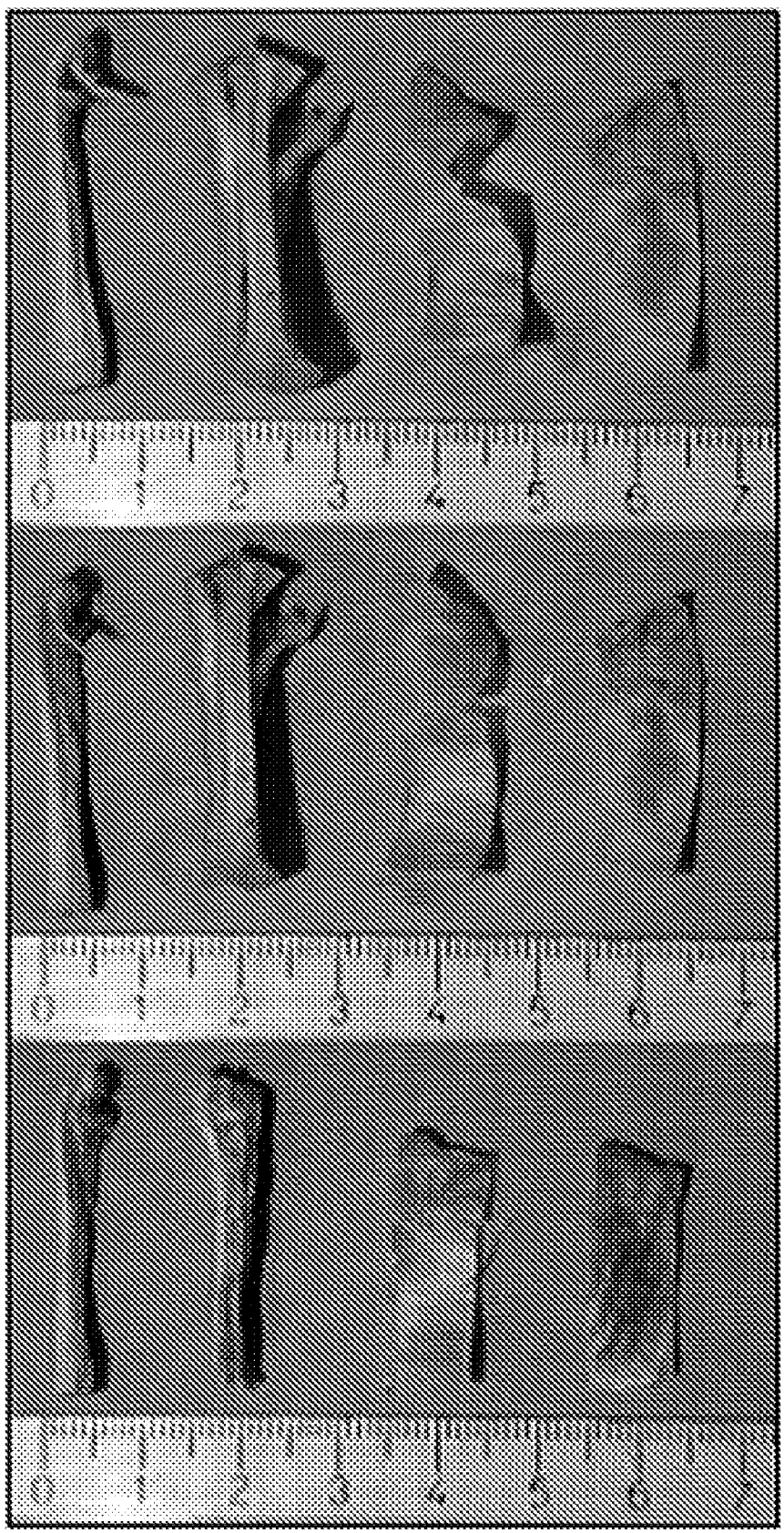
FIG. 3 contains the photograph related to example 7 (rehydration of reimplantation tissues)

Hydration of freeze-dried biological tissues: solution 259 versus spring water. The photograph related to this example is contained in FIG. 3.

With reference to the figure cited above, the first column from the left refers to the "dry" sample, the second column refers to the sample after 15 minutes of treatment, and the third column refers to the sample after 45 minutes of treatment.

Moreover, the first and fourth samples (from the top) were treated with tap water, the second and third samples (again from the top) were treated with solution 259 according to the invention.

The first and second samples (from the top) are samples of Achilles tendon, while the third and fourth samples (from the top) are pericardium.

Dry: fragments of freeze-dried biological tissues (Achilles tendon and pericardial membrane) before immersion in solution 259 and tap water.

T 15': tissue fragments after 15 minutes of immersion at ambient temperature and in static conditions.

T 45': tissue fragments after 45 minutes of immersion at ambient temperature and in static conditions.

Results: the fragments immersed in tap water have a minimum volumetric increase, which is more appreciable in the case of the tendon; the fragments immersed in solution 259 have increased in volume considerably (at least by 3 times). The tendon fibers are further space apart, while the thickness of the pericardium shows an increase by at least three times after 45 minutes of immersion.

Solution 259 has a higher hydration power than tap water, presumably thanks to the particular steric organization of the molecules of $H_2O$ (pentamolecular clusters).

EXAMPLE 8

Figure 4:
FIG. 4, related to example 8, contains a photograph which compares the bacterial lysis activity performed with a conventional acid water (a), with solution 259 (b), and with physiological solution (c)
Figure 4:
Figure 4:
Figure 5:
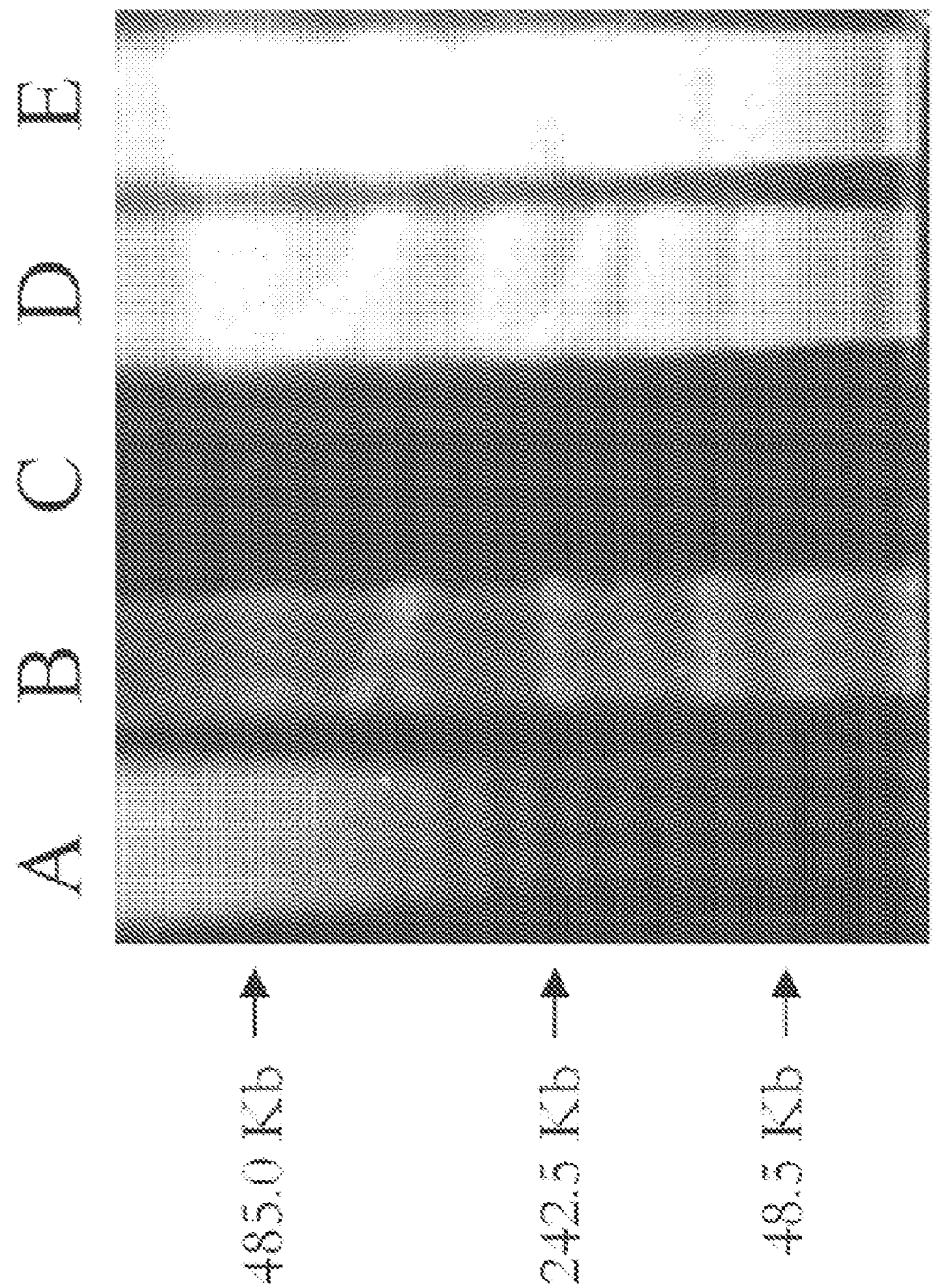
FIG. 5, which again relates to example 8, contains a photograph which compares lysis activity on bacterial DNA. In particular, the experiment is an electrophoresis on agarose gel, where run A) is the standard of DNA molecular weights; run B) is DNA from *P. aeruginosa* treated with conventional electrolytic acid water; run C) is DNA from *P. aeruginosa* treated with solution 259; runs D) and E) are DNA from *P. aeruginosa* treated with physiological solution.

The antibacterial property of solution 259 specifically against P. aeruginosa was tested. FIG. 4 contains a photograph taken by electronic microscope which shows the lysis of the bacterial wall obtained with a conventional acid water (a), with solution 259 (b) and with physiological solution (c). The photograph 5 contains a photograph of a gel electrophoresis of P. aeruginosa DNA after treatment with a conventional acid water (B), with solution 259 (C) and with physiological solution (D). Column (A) is the scale of weights used as reference.

Although only some preferred embodiments of the invention have been described in the text, the person skilled in the art will immediately realize how to obtain other equally advantageous and preferred embodiments.

The disclosures in Italian Patent Applications No. PN2005A000079 and MI2006A001252 from which this application claims priority are incorporated herein by reference.

The invention claimed is:

1. A method of making acid or basic water comprising:
   a) providing a device for the electrolytic treatment of water comprising at least one chamber for the electrolytic treatment of said water and at least one pair of electrodes for said chamber, said electrodes being arranged within said at least one chamber, wherein at least one of the electrodes comprises a surface coating of sintered nanoparticles of one or more metals;
   b) introducing water and a halide salt to said chamber;
   c) electrolyzing said water, thereby producing an acid water fraction and a basic water fraction;
   d) withdrawing said acid water fraction or said basic water fraction as a separate component from said chamber.

2. The method of claim 1, comprising withdrawing an acid water fraction characterized by an ORP greater than 1000, and a pH of greater than 0 and less than or equal to 3.0.

3. The method of claim 1 wherein at least 80% by weight of said nanoparticles have a diameter ranging from 60 to 80 nm.

4. The method of claim 1, wherein said device further comprises a membrane which divides the electrolysis chamber into two half-chambers, wherein said membrane comprises a ceramic material with open porosity, coated with metallic nanoparticles.

5. The method of claim 1, further comprising swapping the polarity between said electrodes.

6. The method of claim 1, wherein said surface coating comprises $ZrO_2$, $ZnO$, $Ru_2O_3$, $IrO_2$ and $Y_2O_3$.

7. A device for the electrolytic treatment of water, comprising at least one chamber for the electrolytic treatment of said water and at least one pair of electrodes for said chamber, said electrodes being arranged within said at least one chamber, wherein at least one of the electrodes comprises a surface coating of sintered nanoparticles of one or more metals.

8. The device of claim 7, further comprising a membrane which divides the electrolysis chamber into two half-chambers, wherein said membrane comprises a ceramic material with open porosity, coated with metallic nanoparticles.

9. The device of claim 7 wherein at least 80% by weight of said nanoparticles have a diameter ranging from 60 to 80 nm.

10. The device of claim 7 wherein said surface coating comprises $ZrO_2$, $ZnO$, $Ru_2O_3$, $IrO_2$ and $Y_2O_3$.

11. The device of claim 7 wherein said surface coating is prepared by:
    a) preparing one or more powders of nanoparticles of one or more metals,
    b) dissolving the one or more powders of nanoparticles in a suitable solvent and in at least such an amount as to be able to dissolve all of said one or more powders, obtaining one or more solutions, and
    c) sintering the one or more solutions onto a metal plate, preferably passivated on its surface.

12. The device of claim 1 wherein:
    a) the one or more powders of nanoparticles is a combination of powders of $ZrO_2$, $ZnO$, $Ru_2O_3$, $IrO_2$ and $Y_2O_3$, where for each powder at least 80% by weight of the particles have a diameter ranging from 60 to 80 nm;
    b) the solvent is a 30% solution by weight of hydrochloric acid in water, and
    c) the sintering step consists in sintering the aqueous solutions of hydrochloric acid obtained from the dissolving step on both faces of a $TiO_2$ plate with a passivated surface and with a thickness ranging from 0.15 to 0.35 mm.

13. The device of claim 11 wherein said sintering occurs according to the following eleven steps:

| Step | Solution | Dosage per unit surface | Sintering time (min) | Sintering temperature (° C.) |
|---|---|---|---|---|
| 1 | $IrO_2$ | 0.2 g/m² | 45 | 450 |
| 2 | $Ru_2O_3$ | 0.2 g/m² | 45 | 450 |
| 3 | $ZnO + Y_2O_3$ (Y at 2 mol) | 0.15 g/m² | 60 | 550 |
| 4 | $IrO_2$ | 0.25 g/m² | 45 | 450 |
| 5 | $Ru_2O_3$ | 0.25 g/m² | 60 | 550 |
| 6 | $ZrO_2 + Y_2O_3$ (Y at 3 mol) | 0.1 g/m² | 60 | 550 |
| 7 | $Ru_2O_3$ | 0.15 g/m² | 60 | 550 |
| 8 | $IrO_2$ | 0.15 g/m² | 60 | 550 |
| 9 | $IrO_2 + Ru_2O_3$ | 0.15 g/m² + 0.15 g/m² | 60 | 600 |
| 10 | $ZrO_2 + Y_2O_3$ (Y at 3 mol) | 0.1 g/m² | 60 | 600 |
| 11 | $IrO_2 + Ru_2O_3$ | 0.15 g/m² + 0.15 g/m² | 60 | 600. |

* * * * *